United States Patent
Lee et al.

(10) Patent No.: US 7,638,322 B2
(45) Date of Patent: Dec. 29, 2009

(54) HYPOXIA INDUCIBLE VEGF PLASMID FOR ISCHEMIC DISEASE

(75) Inventors: Minhyung Lee, Salt Lake City, UT (US); Sung Wan Kim, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 238 days.

(21) Appl. No.: 10/546,115

(22) PCT Filed: Feb. 23, 2004

(86) PCT No.: PCT/US2004/005372

§ 371 (c)(1),
(2), (4) Date: Jun. 27, 2006

(87) PCT Pub. No.: WO2004/076633

PCT Pub. Date: Sep. 10, 2004

(65) Prior Publication Data

US 2007/0149467 A1 Jun. 28, 2007

Related U.S. Application Data

(60) Provisional application No. 60/448,961, filed on Feb. 21, 2003.

(51) Int. Cl.
*C12N 15/00* (2006.01)
(52) U.S. Cl. .................................................. 435/320.1
(58) Field of Classification Search ............... 435/320.1
See application file for complete search history.

(56) References Cited

U.S. PATENT DOCUMENTS 6,548,633 B1 * 4/2003 Edwards et al. ............. 530/300
2003/0104973 A1 * 6/2003 Einat et al. ...................... 514/1

OTHER PUBLICATIONS

Su Hua et al: "Adeno-associated viral vector-mediated hypoxia response element-regulated gene expression in mouse ischemic heart model"; Proceedings of the National Academy of Sciences of USA, National Academy of Science, Washington, DC, US, vol. 99, No. 14, Jul. 9, 2002, pp. 9480-9485.
Jeffrey M. Isner, Myocardial Gene Therapy, 415 Nature 234-239 (2002).
Minhyung Lee, et. al., SP-1 Dependent Regulation of the RTP801 Promotor and Its Application to Hypoxia-Inducible VEGF Plasmid for Ischemic Disease, 21 Pharacautical Research, 736-741 (2004).
Tzipora Shoshani, et. al., Identification of a Novel Hypoxia-Inducible Factor 1-Responsive Gene, RTP801, Involved in Apoptosis, 22 Molecular and Cellular Biology 2282-2293 (2002).
Seppo Yiä-Herttuala, et. al., Cardiovascular Gene Therapy, 355 The Lancet 213-222 (2000).

* cited by examiner

*Primary Examiner*—Brian Whiteman
(74) *Attorney, Agent, or Firm*—Clayton, Howarth & Cannon, P.C.

(57) ABSTRACT

Plasmids useful for treating ischemic disease, such as ischemic heart disease, are described. The plasmids express vascular endothelial growth factor (VEGF) under the control of a promoter (RTP801) that is up-regulated under hypoxic conditions. Pharmaceutical compositions for treating ischemic disease include mixtures of the hypoxia-regulated VEGF plasmids and pharmaceutically acceptable carriers. Methods for treating ischemic disease include administering such pharmaceutical compositions to a person in need of such treatment.

8 Claims, 4 Drawing Sheets

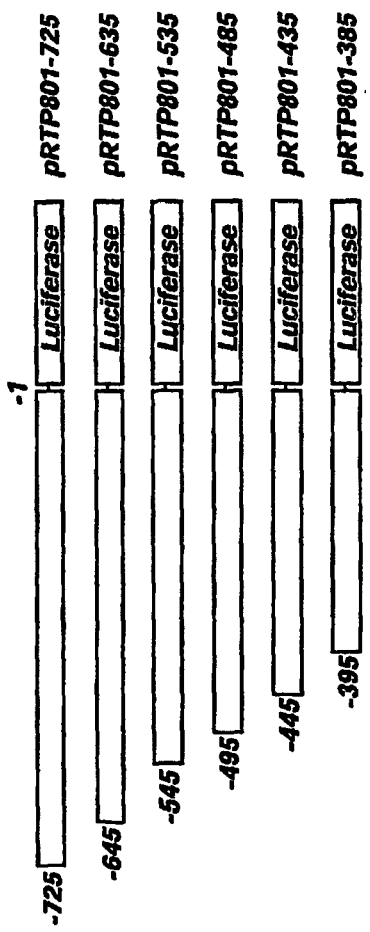
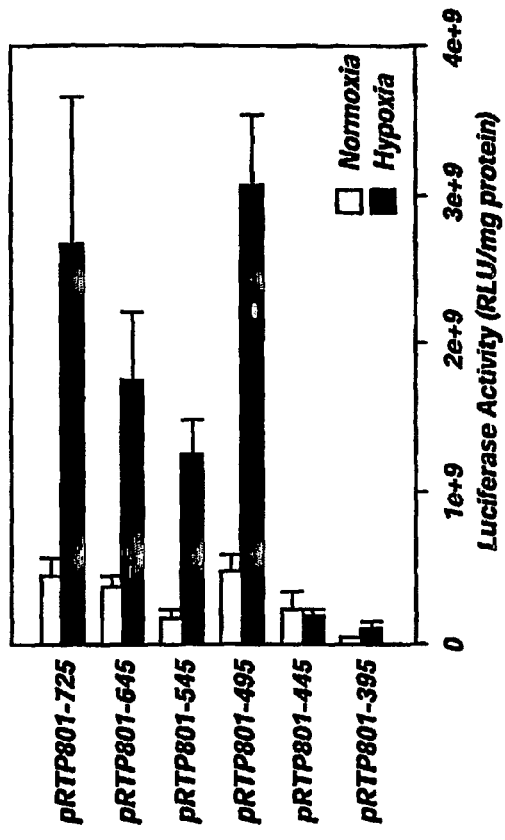
FIG. 1A
FIG. 1B pRTP801-725 (WT)
-495 GGTTCGACTGCGAGCTGCGAGCTTTCTGGGGCTCAATGGAG<u>GGGG</u>CCCCGCCCGCT -446 pRTP801-SP1(-)
-495 GGTTCGACTGCGAGCTGCGAGCTTTCTGGGGCTCAATGGA[TTA]GGGCCCCGCCCGCT -446

HYPOXIA INDUCIBLE VEGF PLASMID FOR ISCHEMIC DISEASE

CROSS-REFERENCE TO RELATED APPLICATIONS

This application is the National Stage of International Application No. PCT/US2004/005372, filed Feb. 23, 2004, which was published in English under PCT Article 21(2), and is hereby incorporated in its entirety, and claims the benefit of U.S. Provisional Application No. 60/448,961, filed Feb. 21, 2003.

STATEMENT REGARDING FEDERALLY SPONSORED RESEARCH OR DEVELOPMENT

This invention was made with government support under Grant No. HL065477 from the National Institutes of Health. The government has certain rights in the invention.

BACKGROUND OF THE INVENTION

This invention relates to gene therapy. More particularly, this invention relates to a plasmid system for increased expression of vascular endothelial growth factor (VEGF) under hypoxia conditions. The plasmid system can be used for treating ischemic disease in a person in need of such treatment, such as a person in need of treatment for ischemic heart disease.

Gene therapy with VEGF is a new treatment of ischemic diseases, such as ischemic heart disease. The delivery of the VEGF gene to ischemic heart has been achieved using naked DNA injection, polymeric carriers, and retrovirus, adenovirus, or adeno-associated virus carriers. M. Azrin, Angiogenesis, protein and gene delivery, 59 Br. Med. Bull. 211-215 (2001); J. M. Isner, Myocardial gene therapy, 415 Nature 234-239 (2002); J. Kastrup et al., Vascular growth factor and gene therapy to induce new vessels in the ischemic myocardium. Therapeutic angiogenesis, 35 Scand. Cardiovasc. J. 291-296 (2001). Naked DNA injection is safe, since it does not induce cytotoxicity or severe immune response. Previous reports have shown that naked plasmid delivery of the VEGF gene is effective in the treatment of ischemic myocardium. J. F. Symes et al., Gene therapy with vascular endothelial growth factor for inoperable coronary artery disease, 68 Ann. Thorac. Surg. 830-836, discussion 836-837 (1999); P. R. Vale et al., Left ventricular electromechanical mapping to assess efficacy of phVEGF(165) gene transfer for therapeutic angiogenesis in chronic myocardial ischemia, 102 Circulation 965-974 (2000); C. Sylven et al., Myocardial Doppler tissue velocity improves following myocardial gene therapy with VEGF-A165 plasmid in patients with inoperable angina pectoris, 12 Coron. Artery Dis. 239-243 (2001). However, injection of naked plasmid suffers from low efficiency of gene expression. J. M. Isner, supra.

To improve efficiency of plasmid delivery, polymeric gene carriers have been developed. These polymeric gene carriers include TerplexDNA and water-soluble lipopolymer (WSLP). D. G. Affleck et al., Augmentation of myocardial transfection using TerplexDNA: a novel gene delivery system, 8 Gene Ther. 349-353 (2001); M. Lee et al., Hypoxia-inducible VEGF gene delivery to ischemic myocardium using water-soluble lipopolymer, 10 Gene Ther. 1535-1542 (2003). These polymeric gene carriers increased the transfection efficiency to myocardium up to tenfold. In addition, the duration of gene expression was prolonged compared to naked DNA. The prolonged duration of gene expression by polymeric carriers may be due to the ability of the carriers to protect DNA from nucleases. However, these polymeric carriers may be cytotoxic to cells and still have lower transfection efficiency than viral carriers.

Another approach to gene delivery is to use retrovirus, adenovirus, or adeno-associated virus as a gene delivery vector. Virus-mediated gene transfer showed high gene transfer and expression activities. It is generally accepted that a viral carrier is the most efficient way to transfer therapeutic genes. However, virus-mediated gene transfer may lead to immunogenicity or host chromosomal integration, suggesting possible mutagenesis. M. Azrin, supra. In addition, the production of viral particles for encapsulating the DNA is not as cost-effective as that of naked DNA or polymeric carriers.

Therefore, each delivery method has its own advantages and disadvantages, and the selection of a gene carrier is largely dependent on its availability and the target disease.

Another concern with respect to gene therapy using VEGF is the gene regulation system. Currently, VEGF is the most effective therapeutic gene for neo-vascularization. J. M. Isner, supra. Previously, it was reported that both VEGF and its receptors were upregulated in ischemic tissues. E. Brogi et al., Hypoxia-induced paracrine regulation of vascular endothelial growth factor receptor expression, 97 J. Clin. Invest. 469-476 (1996). Therefore, it was suggested that ischemia is necessary for VEGF to exert its effects. J. S. Lee & A. M. Feldman, Gene therapy for therapeutic myocardial angiogenesis: a promising synthesis of two emerging technologies, 4 Nature Med. 739-742 (1998). However, Springer et al. proved that exogenously delivered VEGF could exert a physiological effect in normal, non-ischemic tissue. M. L. Springer et al., VEGF gene delivery to muscle: potential role for vasculogenesis in adults, 2 Mol. Cell 549-558 (1998). In addition, unregulated continuous expression of VEGF is associated with formation of endothelial cell-derived intramural vascular tumors. R. J. Lee et al., VEGF gene delivery to myocardium: deleterious effects of unregulated expression, 102 Circulation 898-901 (2000). This suggested that VEGF expression must be regulated. Therefore, an erythropoietin (Epo) enhancer was used to enhance VEGF gene expression locally in ischemic tissues. It was shown that the Epo enhancer and the SV40 promoter enhanced VEGF gene expression under hypoxia condition in human embryonic kidney 293 cells in vitro and in rabbit ischemic myocardium in vivo. M. Lee et al., supra. In addition, Su et al. proved that a hypoxia-responsive element (HRE) mediated VEGF expression in ischemic myocardium, using adeno-associated virus as a gene carrier. H. Su et al., Adeno-associated viral vector-mediated hypoxia response element-regulated gene expression in mouse ischemic heart model, 99 Proc. Nat'l Acad. Sci. USA 9480-9485 (2002). In this trial, the VEGF gene was regulated by the hypoxia response element (HRE) and the SV40 promoter. This regulated VEGF expression system should be useful for safer VEGF gene therapy, minimizing unwanted side effects.

In view of the foregoing, it will be appreciated that providing a plasmid for gene therapy of ischemic disease, wherein the plasmid expresses VEGF under regulated control and can be delivered with a polymeric carrier, would be a significant advancement in the art.

BRIEF SUMMARY OF THE INVENTION

An illustrative embodiment of the present invention relates to the plasmid pRTP801-VEGF (SEQ ID NO:13), which expresses VEGF under the control of the RTP801 promoter, which is upregulated under hypoxic conditions.

Other illustrative embodiments of the invention include the following plasmids: pRTP801-725, pRT801-645, pRTP801-545, pRTP801-495, pRTP801-445, pRTP801-395, and pRTP801-SP1(−).

Another aspect of the invention relates to a plasmid comprising a hypoxia-regulated promoter element operationally configured adjacent to an expression cassette encoding vascular endothelial growth factor (VEGF) such that expression of vascular endothelial growth factor in a suitable cell is higher under hypoxia as compared to normoxia. In an illustrative embodiment of this invention, the hypoxia-regulated promoter element comprises an RTP-801 promoter.

Another aspect of the invention relates to a composition comprising a mixture of pRTP801-VEGF (SEQ ID NO:13) and a pharmaceutically acceptable gene delivery carrier.

Still another aspect of the invention relates to a method for treating ischemic disease comprising administering to a patient in need of treatment for ischemic disease a composition comprising a mixture of pRTP801-VEGF (SEQ ID NO:13) and a pharmaceutically acceptable gene delivery carrier.

BRIEF DESCRIPTION OF THE SEVERAL VIEWS OF THE DRAWINGS

FIG. 1A shows schematic representations of the structures of pRTP801 luciferase reporter vectors containing various lengths of 5'-flanking regions of the human RTP801 promoter.

FIG. 1B shows hypoxia responsiveness of the 5'-flanking region of the RTP801 promoter: the reporter constructs were transiently transfected into human embryonic kidney 293 cells, and the cells were incubated for 24 hrs under normoxic (open bars) or hypoxic (closed bars) conditions, and luciferase activity was determined.

DETAILED DESCRIPTION

Figures 2A, 2B:
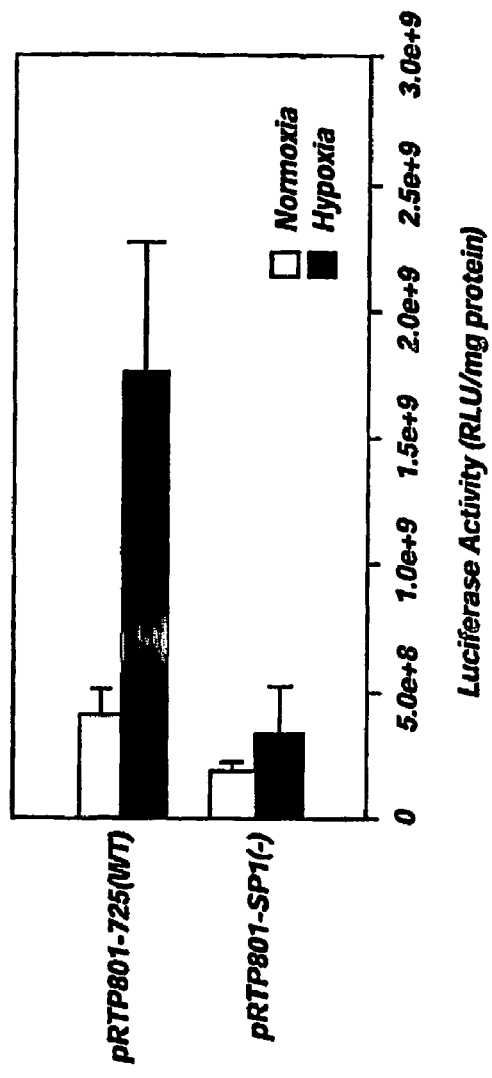
FIG. 2A shows the nucleotide sequences of the wild type RTP801 promoter of pRTP801-725 between nucleotides -495 and -446 (SEQ ID NO:11; the Sp1 consensus sequence is underlined) and the corresponding region of pRTP801-Sp1(−) (SEQ ID NO:12; the mutation position is enclosed in a box).
FIG. 2B shows the effect of mutation in the Sp1 element in the RTP801 promoter on promoter activity: plasmids pRTP801-725 and pRTP801-Sp1(−) were transiently transfected into human embryonic kidney 293 cells, the transfected cells were incubated for 24 hrs under hypoxic (closed bars) or normoxic (open bars) conditions, and then luciferase activity was determined.

Before the hypoxia inducible gene expression system and methods are disclosed and described, it is to be understood that this invention is not limited to the particular configurations, process steps, and materials disclosed herein, as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. For example, reference to a method of treating a disease comprising administering "a plasmid" includes reference to two or more of such plasmids, reference to a plasmid comprising "an expression cassette" includes reference to two or more of such expression cassettes, and reference to "the pharmaceutically acceptable gene delivery carrier" includes reference to two or more of such gene delivery carriers.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

As used herein, "hypoxia" means a reduction in oxygen supply to tissues below physiological levels despite adequate perfusion of the tissues by blood. In other words, hypoxia relates to an oxygen deficiency in bodily tissues. In relation to in vitro experiments, "hypoxia" means that the amount of oxygen supplied to cultured cells was significantly below that of air, for example, about 1% $O_2$ as compared to about 20% $O_2$ in air.

As used herein, "normoxia" means a normal or physiological level of oxygen supply to bodily tissues. In relation to in vitro experiments, "normoxia" means that the amount of oxygen supplied to cultured cells was the same as that of air (about 20% oxygen).

As used herein, "administering" and similar terms mean delivering a composition, such as a mixture of a plasmid and a carrier, to an individual being treated such that the composition is delivered to the parts of the body where the plasmid can transfect target cells. Thus, the composition is illustratively administered to the individual by systemic administration, typically by subcutaneous, intramuscular, or intravenous administration, or intraperitoneal administration. However, it is well known in the art that delivery options for implementing myocardial gene transfer include epicardial, endocardial, intracoronary, retroperfusion, and intrapericardial routes of administration. J. M. Isner, supra. All type of vectors can be delivered by intramyocardial injection via the epicardial and endocardial routes of administration and by intrapericardial injection. Intracoronary and retroperfusion delivery may not be appropriate for non-viral gene transfer or other methods of gene transfer owing to intracirculatory degradation of plasmid DNA unprotected by a viral vector or other vector.

The term "pharmaceutically acceptable" refers to molecular entities and compositions that are physiologically tolerable and do not typically produce an allergic or similar untoward reaction, such as gastric upset, dizziness, and the like, when administered to a human. Illustratively, the term "pharmaceutically acceptable" means approved by a regulatory agency of the Federal or a state government or listed in the U.S. Pharmacopeia or other generally recognized pharmacopeia for use in animals, and more particularly in humans.

The term "gene delivery carrier" and similar terms refer to refer to both viral and non-viral vectors for delivery of nucleic acids. As discussed above, viral vectors, including adenovirus, adeno-associated virus, retrovirus, and lentivirus, are generally viewed as the most effective means for transferring therapeutic genes. Naked DNA is typically delivered in an aqueous carrier, such as water, buffer, or the like. Polymeric carriers that have been used for delivery of therapeutic nucleic acids include cationic liposomes, H. M. Temin, Safety considerations in somatic gene therapy of human disease with retrovirus vectors, 1 Human Gene Therapy 111-123 (1990); mixtures of hydrophobized cationic polymers and lipoprotein ("Terplex DNA"), U.S. Pat. No. 5,679,559; water-soluble lipopolymer (WSLP). D. G. Affleck et al., supra; and the like.

Angiogenic gene therapy using vascular endothelial growth factor (VEGF) is a new treatment for ischemic disease. To be safe and effective, gene therapy with VEGF must be regulated, and VEGF expression should be enhanced locally in ischemic tissue. In this study, the cis-regulatory element responsible for hypoxia induction of the RTP801 promoter was identified. To identify the cis-regulatory element, the RTP801 promoter was analyzed by various methods. In a luciferase assay, the region between -495 and -445 was shown to be responsible for hypoxia-induced transcription. In this region, there was a potential Sp1 binding element. Mutation of the Sp1 site reduced the hypoxia-induced transcription of the RTP801 promoter. In addition, co-transfection with an antisense Sp1 oligonucleotide decreased the promoter activity. These results suggest that hypoxia induction of the RTP801 promoter is mediated by Sp1.

In addition, the RTP801-VEGF (SEQ ID NO:13) plasmid was evaluated as a therapeutic plasmid. The RTP801 promoter was shown to be inducible under hypoxia conditions in various cell lines, which is a desirable characteristic for a promoter to be used in gene therapy applications. These results showed that the RTP801 promoter was active and inducible in 293 (human embryonic kidney) cells, NIH3T3 (mouse fibroblast) cells, HepG2 (human hepatocyte) cells, A7R5 (rat smooth muscle) cells, and HUVEC (human umbilical vascular endothelial) cells. The plasmid, pRTP801-VEGF, was constructed by insertion of the RTP801 promoter into a VEGF-encoding plasmid. The resulting pRTP801-VEGF plasmid exhibited stronger basal and induced levels of VEGF expression than pEpo-SV-VEGF, which contained the Epo (erythropoietin) enhancer and the SV40 promoter system. In addition, the VEGF expression by pRTP801-VEGF was induced under hypoxic conditions. Therefore, with strong basal promoter activity and induction under hypoxic conditions, pRTP801-VEGF can be used for VEGF gene therapy for ischemic disease.

Ischemic disease can be treated by administering pRTP801-VEGF to a person in need of such treatment. The pRTP801-VEGF plasmid is typically mixed with a pharmaceutically acceptable gene delivery carrier. In the case of delivery of naked DNA, the plasmid is mixed with water, buffer, or the like. In the case of delivery using a polymeric carrier, the plasmid is mixed with a selected polymeric carrier. In the case of delivery using liposomes, the plasmid is mixed with the liposomes such that the DNA is incorporated into the liposomes. The plasmid-containing mixture is then administered to the patient. Illustratively, when treating a person for ischemic heart disease, the plasmid-containing mixture is injected by intramyocardial injection procedures known in the art. A proportion of cells exposed to the plasmid take up the plasmid and express VEGF. Whereas genes encoding proteins that must remain intracellular to achieve a biological effect have to be delivered to a relatively large target population of cells to correct the underlying pathogenic defect, genes encoding proteins that are naturally secreted can achieve favorable effects when limited numbers of cells are transfected, provided that the transfected cells secrete substantial amounts of the gene product. VEGF, as expressed in cells, contains a signal sequence and, thus, is actively secreted from transfected cells. The secreted VEGF exerts its paracrine effect to modulate the bioactivity of several target cells.

Plasmids pRTP801-725, pRTP801-645, pRTP801-545, pRTP801-495, pRTP801445, pRTP801-395, and pRTP801-SP1(-) are useful for making of plasmid constructs for expression of gene products that would be induced or not induced by hypoxia. For example, plasmids pRTP801-725, pRTP801-645, pRTP801-545, and pRTP801-495 contain various lengths of the RTP801 promoter region, and all of these plasmids exhibit hypoxia inducibility. Any of these promoter regions could be used in constructing a plasmid that would be effective for expression of a selected gene product, which expression would be induced under hypoxic conditions. For example, any of these promoter regions could be used in making, according to the procedures of Example 10, a plasmid that would exhibit hypoxia-inducible expression of VEGF. By way of further example, plasmids pRTP801-445 and pRTP801-395 contain various lengths of the RTP801 promoter region that have been resected such that they do not direct hypoxia-inducible expression of a gene product. Therefore, either of these promoter regions could be used in making, according to the procedures of Example 10, a plasmid that would express VEGF at a relatively low level, which expression would not be induced under hypoxia. Similarly, plasmid pRTP801-SP1(-) contains a mutated RTP801 promoter region that does not direct hypoxia-inducible expression of a gene product. Therefore, this promoter region could be used in making, according to the procedures of Example 10, a plasmid that would express VEGF at a relatively low level, which expression would not be induced under hypoxia

EXAMPLE 1

Construction of pRTP801-725

The RTP801 promoter was cloned by PCR using genomic DNA from HepG2 (human liver) cells according to procedures well known in the art. The HepG2 cells were obtained from ATCC (Manassas, Va.) and were maintained in Dulbecco's modified Eagle medium (DMEM) supplemented with 10% fetal bovine serum (FBS) in a 5% $CO_2$ incubator. The genomic DNA was extracted from HepG2 cells using the Qiagen DNeasy Tissue system (Qiagen, Valencia, Calif.). The sequences of the forward and backward primers for amplification of the RTP801 promoter were SEQ ID NO:2 and SEQ D NO:3, respectively. BglII and HindIII restriction endonuclease sites were engineered into the forward and backward primers, respectively, for convenience in cloning. The PCR-amplified RTP801 (725 base) fragment was digested with BglII and HindIII restriction endonucleases and purified by gel electrophoresis and elution. The pGL3-promoter plasmid (SEQ ID NO:1) was purchased from Promega (Madison, Wis.). The SV40 promoter was eliminated from the pGL3-promoter plasmid by digestion with BglII and HindIII restriction endonucleases, and the plasmid backbone was purified by gel electrophoresis and elution. The RTP801 promoter fragment was ligated into the BglII- and HindIII-digested pGL3-promoter plasmid, resulting in construction of pRTP801-725. The integrity of the cloned RTP801 promoter was confirmed by DNA sequencing according to procedures well known in the art.

EXAMPLE 2

Construction of pRTP801-645

A deletion in the 5'-region of the RTP801 promoter was made by PCR. The backward primer (SEQ ID NO:3) was the same as in Example 1. The forward primer was SEQ ID NO:4, which contained a BglII restriction endonuclease site. The PCR fragment was subcloned into the pGL3-promoter vector using the procedure of Example 1. The resulting plasmid was named pRTP801-645, because DNA upstream of nucleotide -645 was deleted. The integrity of the promoter fragment was confirmed by DNA sequencing.

EXAMPLE 3

Construction of pRTP801-545

Another deletion in the 5'-region of the RTP801 promoter was made by PCR. The backward primer (SEQ ID NO:3) was the same as in Example 1. The forward primer was SEQ ID NO:5, which contained a BglII restriction endonuclease site. The PCR fragment was subcloned into the pGL3-promoter vector using the procedure of Example 1. The resulting plasmid was named pRTP801-545, because DNA upstream of nucleotide -545 was deleted. The integrity of the promoter fragment was confirmed by DNA sequencing.

EXAMPLE 4

Construction of pRTP801-495

Another deletion in the 5'-region of the RTP801 promoter was made by PCR. The backward primer (SEQ ID NO:3) was the same as in Example 1. The forward primer was SEQ ID NO:6, which contained a BglII restriction endonuclease site. The PCR fragment was subcloned into the pGL3-promoter vector using the procedure of Example 1. The resulting plasmid was named pRTP801-495, because DNA upstream of nucleotide -495 was deleted. The integrity of the promoter fragment was confirmed by DNA sequencing.

EXAMPLE 5

Construction of pRTP801-445

Another deletion in the 5'-region of the RTP801 promoter was made by PCR. The backward primer (SEQ ID NO:3) was the same as in Example 1. The forward primer was SEQ ID NO:7, which contained a BglII restriction endonuclease site. The PCR fragment was subcloned into the pGL3-promoter vector using the procedure of Example 1. The resulting plasmid was named pRTP801-445, because DNA upstream of nucleotide -445 was deleted. The integrity of the promoter fragment was confirmed by DNA sequencing.

EXAMPLE 6

Construction of pRTP801-395

Another deletion in the 5'-region of the RTP801 promoter was made by PCR. The backward primer (SEQ ID NO:3) was the same as in Example 1. The forward primer was SEQ ID NO:8, which contained a BglII restriction endonuclease site. The PCR fragment was subcloned into the pGL3-promoter vector using the procedure of Example 1. The resulting plasmid was named pRTP801-395, because DNA upstream of nucleotide -395 was deleted. The integrity of the promoter fragment was confirmed by DNA sequencing.

EXAMPLE 7

Deletion Analysis of the Responsiveness of the RTP801 Promoter to Hypoxia

To identify the region necessary for hypoxia induction in the RTP801 promoter, various fragments of the 5'-flanking region of the RTP801 promoter up to 725 bp upstream from the ATG translation initiation codon were cloned into the luciferase reporter gene plasmid (FIG. 1; Examples 1-6).

These constructs were transfected into human embryonic kidney 293 cells using polyethylenimine (PEI; 25,000 Da) as a gene carrier. The 293 cells were maintained in DMEM supplemented with 10% FBS in a 5% $CO_2$ incubator. For the transfection assays, the cells were seeded at a density of $5.0 \times 10^5$ cells/well in a 35-mm cell culture dish (Falcon Co., Becton Dickenson, Franklin Lakes, N.J.) 24 hrs before transfection. Plasmid/PEI complexes were prepared at a 5/1 N/P ratio and incubated for 30 min at room temperature. The cells were washed twice with serum-free medium, and then 2 ml of fresh serum-free medium was added. The plasmid/PEI complex was added to each dish. The cells were then incubated for 4 hrs at 37° C. in a 5% $CO_2$ incubator. After 4 hrs, the transfection mixtures were removed and 2 ml of fresh medium containing FBS was added.

The transfected cells were incubated under hypoxia (1% $O_2$) or normoxia condition (20% $O_2$) for 20 hrs. After incubation, the cells were twice washed with phosphate-buffered saline (PBS), and 150 µl of reporter lysis buffer (Promega, Madison, Wis.) was added to each well. After 15 min of incubation at room temperature, the cells were harvested and transferred to microcentrifuge tubes. After 15 s of vortexing, the cells were centrifuged at 11,000 rpm for 3 min. The extracts were transferred to fresh tubes and stored at −70° C. until use. The protein concentrations of the extracts were determined using a BCA protein assay kit (Pierce, Iselin, N.J.). Luciferase activity was measured in terms of relative light units (RLU) using a 96-well plate Luminometer (Dynex Technologies Inc, Chantilly, Va.). The luciferase activity was monitored and integrated over a period of 60 s. The final values of luciferase were reported in terms of RLU/mg total protein.

As a result, the activities of pRTP801-725, pRTP801-645, pRTP801-545, and pRTP801-495 increased under hypoxic conditions. However, the activity of pRTP801-445 did not increase (FIG. 1). These results indicate that the cis-regulatory element that responds to hypoxia lies between nucleotides -495 and -445. The sequence in this region is SEQ ID NO:11.

EXAMPLE 8

Role of Sp1 in the Induction of the RTP801 Promoter

Sequence analysis showed that there was a potential Sp1 consensus binding site in the region between -495 and -445. To evaluate the effect of mutation of this Sp1 binding site, site-directed mutagenesis was performed. The sequence of GGCG (−459~462) was replaced with the sequence of TTAT, resulting in construction of pRTP801-SP1(−) (FIG. 2A; SEQ ID NO:12). The Sp1 mutant constructs were generated using the QuickChange site-directed mutagenesis kit (Stratagene, La Jolla, Calif.) using the pRTP801-725 construct as a template. The sequences of the mutated Sp1 oligonucleotides used were SEQ ID NO:9 (Sp1 mutant, upstrand) and SEQ ID NO:10 (downstrand).

Plasmids pRTP801-725 (wild-type) and pRTP801-SP1(−) were transfected into 293 cells, and the transfected cells were incubated under hypoxic or normoxic conditions, according to the procedures of Example 7. After incubation, luciferase activity was measured, also according to the procedure of Example 7. In cells transfected with pRTP801-SP1(−), hypoxia induction of the RTP801 promoter was decreased as compared to the cells transfected with pRTP801-725 (FIG. 2B). Therefore, this result indicates that the Sp1 element in the RTP801 promoter plays an important role in hypoxia induction of the RTP801 promoter.

Figure 3:
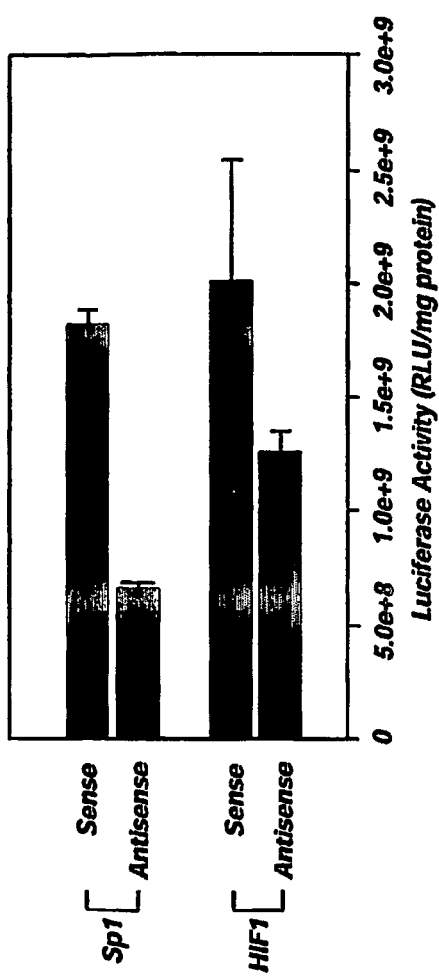
FIG. 3 shows the role of Sp1 in the hypoxia-inducibility of the RTP801 promoter: plasmid pRTP801-725 was transfected into human embryonic kidney 293 cells in the presence of Sp1 sense, Sp1 antisense, HIF-1α sense, or HIF-1α antisense oligonucleotides, the transfected cells were exposed to hypoxic or normoxic conditions for 24 hrs, and then luciferase activity was determined.

Another approach to showing that Sp1 is important for hypoxia induction of the RTP801 promoter was to use antisense oligonucleotides directed against Sp1 (FIG. 3). The antisense Sp1 oligonucleotides were co-transfected with pRTP801-725 into 293 cells. As a control, the sense Sp1 oligonucleotides were co-transfected with pRTP801-725. The antisense HIF-1 or sense HIF-1 oligonucleotides were also co-transfected with pRTP801-725 to evaluate the effect of HIF-1. The transfected cells were incubated under hypoxic condition for 20 hrs. Cell extracts were prepared from the cells and the luciferase activity were measured. As a result, in the cells transfected with the antisense Sp1 oligonucleotides the activity of the RTP801 promoter was reduced compared to the cells transfected with sense Sp1 oligonucleotides (FIG. 3). This result suggests that Sp1 mediates hypoxia induction of the RTP801 promoter. On the other hand, in the cells transfected with the antisense HIF-1 oligonucleotides, the activity of the RTP801 promoter decreased slightly, suggesting the role of HIF-1.

EXAMPLE 9

Transcriptional Induction of the RTP801 Promoter in Various Cell Lines

To apply the RTP801 promoter to gene therapy in various organs, it was important to confirm that the RTP801 promoter did not have cell-type specificity in gene expression. To test whether the RTP801 promoter can be induced in various types of cells, HUVEC (human umbilical vascular endothelial cell), A7R5 (rat smooth muscle cell), NIH3T3 (mouse fibroblast cell), and HepG2 (human hepatocyte) cells were transfected with pRTP801-725. The A7R5, NIH3T3, and HUVEC cells were purchased from ATCC. The A7R5, NIH3T3, and HepG2 cells were maintained in DMEM supplemented with 10% FBS in a 5% $CO_2$ incubator. The HUVEC cells were maintained in F-12K medium supplemented with 10% FBS, 2 mM L-glutamine, 1.5 mg/ml sodium bicarbonate, 0.1 mg/ml heparin, and 0.04 mg/ml endothelial cell growth supplement (ECGS) in a 5% $CO_2$ incubator.

Figure 4:
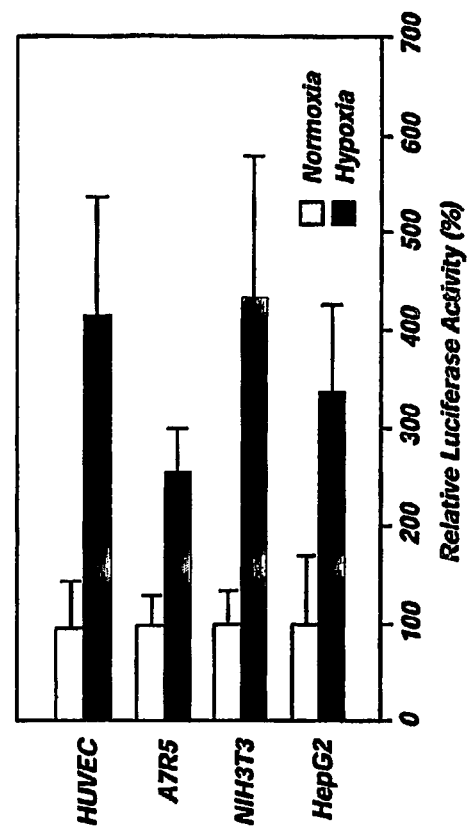
FIG. 4 shows hypoxia-inducibility of the RTP801 promoter in various cell lines: the pRTP801-725 plasmid was transfected into HUVEC, A7R5, NIH3T3, and HepG2 cells, the transfected cells were exposed to hypoxic (closed bars) or normoxic (open bars) conditions for 24 hrs, and then luciferase activity was determined.

Luciferase assay, which was carried out according to the procedure of Example 7, showed that the RTP801 promoter induced the gene expression under hypoxia condition by about 2~4 fold (FIG. 4). Therefore, the RTP801 promoter can be induced by hypoxia in various cell types.

EXAMPLE 10

VEGF Expression Mediated the RTP801 Promoter

Figure 5:
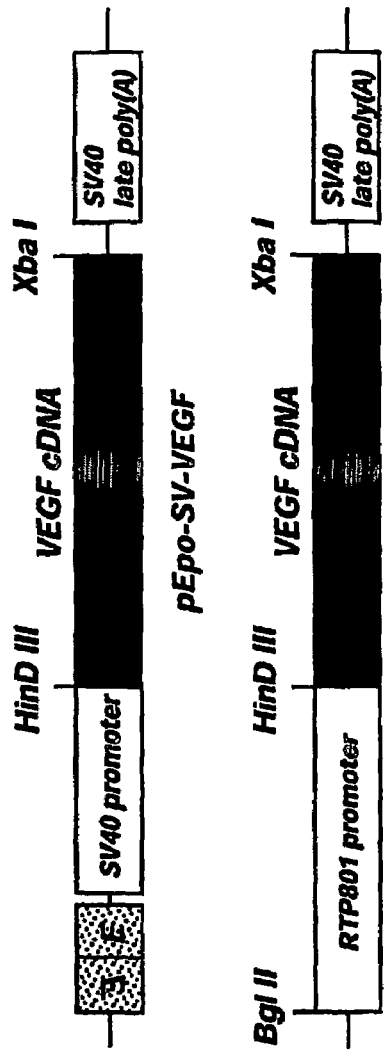
FIG. 5 shows the structures of pEpo-SV-VEGF and pRTP801-VEGF: in pEpo-SV-VEGF two copies of the Epo enhancer (E) were inserted upstream of the SV40 promoter, and in pRTP801-VEGF the RTP801 promoter was inserted upstream of the VEGF cDNA.
Figure 6:
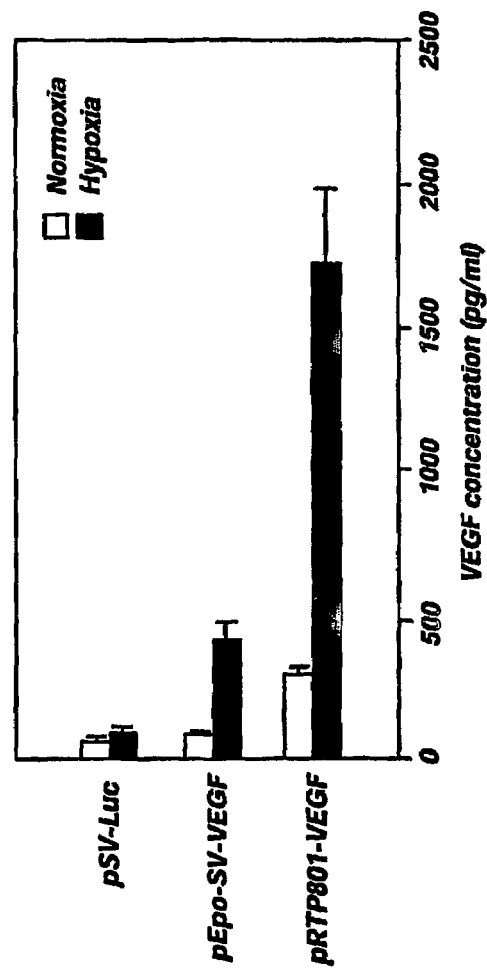
FIG. 6 shows induction of VEGF expression: plasmids pEpo-SV-VEGF, pRTP801-VEGF, and pSV-Luc (negative control) were transfected into human embryonic kidney 293 cells, the cells were exposed to hypoxic (closed bars) or normoxic (open bars) conditions for 24 hrs, and then the cell culture media were collected and the VEGF concentration was determined by ELISA.

To apply the RTP801 promoter to VEGF gene therapy, plasmid pRTP801-VEGF (SEQ ID NO:13) was constructed by insertion of the RTP801 promoter upstream of the VEGF cDNA (FIG. 5). The pEpo-SV-VEGF plasmid, which had been constructed previously, was used as a positive control plasmid. M. Lee et al., supra. The previous report showed that pEpo-SV-VEGF plasmid induced VEGF gene expression in hypoxic cells after 24 hrs of hypoxia incubation. Plasmids pRTP801-VEGF and pEpo-SV-VEGF were transfected into human embryonic kidney 293 cells using PEI as a gene carrier, according to the procedure of Example 7. Plasmid pCMV-Luc (Stratagene, La Jolla, Calif.) was transfected as a negative control. The transfected cells were incubated under hypoxia for 20 hrs. The cell culture media were collected, and the expression level of the VEGF gene was measured by ELISA.

ELISA was performed using ChemiKine human vascular endothelial growth factor sandwich ELISA kit (Chemicon, Temecula, Calif.). One-hundred-microliter samples were added into designated wells of a microtiter plate. Twenty five microliters of biotinylated rabbit anti-human VEGF polyclonal antibody was added to each well, and the plate was incubated at room temperature for 3 hrs. After incubation, the plate was washed 7 times with wash buffer. Fifty microliters of streptavidin-alkaline phosphatase was added to each well, and the plate was incubated at room temperature for 45 min. After the incubation, the plate was washed 7 times with wash buffer. The substrate was then added to the wells, and absorbance was measured at 490 mn. Comparison of VEGF concentrations was made by Student's t-test. P values under 0.05 were deemed to be statistically significant.

As a result, VEGF expression level was induced in both the pRTP801-VEGF and pEpo-SV-VEGF transfected cells (FIG.

6). However, the basal or induction level of VEGF expression under control of the RTP801 promoter was higher than that under control of the Epo enhancer-SV40 promoter.

SEQUENCE LISTING FREE TEXT

SEQ ID NO:1, numeric identifier 223: pGL3-Promoter Vector.
SEQ ID NO:2, numeric identifier 223: RTP801 forward primer.
SEQ ID NO:3, numeric identifier 223: RTP801 backward primer.
SEQ ID NO:4, numeric identifier 223: RTP801-645 forward primer.
SEQ ID NO:5, numeric identifier 223: RTP801-545 forward primer.
SEQ ID NO:6, numeric identifier 223: RTP801-495 forward primer.
SEQ ID NO:7, numeric identifier 223: RTP801-445 forward primer.
SEQ ID NO:8, numeric identifier 223: RTP801-395 forward primer.
SEQ ID NO:9, numeric identifier 223: Sp1 mutant upstrand primer.
SEQ ID NO:10, numeric identifier 223: Sp1 downstrand primer.
SEQ ID NO:13, numeric identifier 223: Plasmid pRTP801-VEGF.

The subject matter claimed is:

1. A plasmid comprising a truncated promoter element from a human RTP-801 nucleotide sequence, including its Sp-1 binding element, operationally configured adjacent to a vascular endothelial growth factor coding sequence.

2. A plasmid comprising a hypoxia-regulated, truncated human RTP-801 promoter element, including its Sp-1 binding element, operationally configured adjacent to an expression cassette encoding vascular endothelial growth factor such that, after delivery of the plasmid into a suitable mammalian cell, higher expression of vascular endothelial growth factor is achieved under hypoxia than under normoxia.

3. A composition comprising a mixture of (1) a plasmid comprising a truncated promoter element from a human RTP-801 nucleotide sequence, including its Sp-1 binding element, operationally configured adjacent to a vascular endothelial growth factor coding sequence, and (2) a pharmaceutically acceptable gene delivery carrier.

4. The plasmid of claim 1, comprising SEQ ID NO:13.

5. The plasmid of claim 2 wherein the truncated human RTP-801 promoter element comprises about 495-725 nucleotides upstream from the RTP-801 translation initiation codon.

6. The composition of claim 3, wherein the plasmid comprises SEQ ID NO:13.

7. A composition comprising a mixture of (1) a plasmid comprising a hypoxia-regulated, truncated human RTP-801 promoter element, including its Sp-1 binding element, operationally configured adjacent to an expression cassette encoding vascular endothelial growth factor such that, after delivery of the plasmid into a suitable mammalian cell, higher expression of vascular endothelial growth factor is achieved under hypoxia than under normoxia, and (2) a pharmaceutically acceptable gene delivery carrier.

8. The composition of claim 7 wherein the truncated human RTP-801 promoter element comprises about 495-725 nucleotides upstream from the RTP-801 translation initiation codon.

* * * * *

SEQUENCE LISTING

```
<160> NUMBER OF SEQ ID NOS: 13

<210> SEQ ID NO 1
<211> LENGTH: 5010
<212> TYPE: DNA
<213> ORGANISM: Artificial
<220> FEATURE:
<223> OTHER INFORMATION: pGL3-Promoter Vector

<400> SEQUENCE: 1
ggtaccgagc tcttacgcgt gctagcccgg gctcgagatc tgcgatctgc atctcaatta      60
gtcagcaacc atagtcccgc ccctaactcc gcccatcccg cccctaactc cgcccagttc     120
cgcccattct ccgccccatc gctgactaat ttttttatt tatgcagagg ccgaggccgc     180
ctcggcctct gagctattcc agaagtagtg aggaggcttt tttggaggcc taggcttttg     240
caaaaagctt ggcattccgg tactgttggt aaagccacca tggaagacgc caaaaacata     300
aagaaaggcc cggcgccatt ctatccgctg aagatggaa ccgctggaga gcaactgcat     360
aaggctatga agagatacgc cctggttcct ggaacaattg cttttacaga tgcacatatc     420
gaggtggaca tcacttacgc tgagtacttc gaaatgtccg ttcggttggc agaagctatg     480
aaacgatatg ggctgaatac aaatcacaga atcgtcgtat gcagtgaaaa ctctcttcaa     540
ttctttatgc cggtgttggg cgcgttattt atcggagttg cagttgcgcc cgcgaacgac     600
atttataatg aacgtgaatt gctcaacagt atgggcattt cgcagcctac cgtggtgttc     660
gtttccaaaa aggggttgca aaaattttg aacgtgcaaa aaagctccc aatcatccaa     720 aaaattatta tcatggattc taaaacggat taccagggat ttcagtcgat gtacacgttc     780
gtcacatctc atctacctcc cggttttaat gaatacgatt ttgtgccaga gtccttcgat     840
agggacaaga caattgcact gatcatgaac tcctctggat ctactggtct gcctaaaggt     900
gtcgctctgc ctcatagaac tgcctgcgtg agattctcgc atgccagaga tcctattttt     960
ggcaatcaaa tcattccgga tactgcgatt ttaagtgttg ttccattcca tcacggtttt    1020
ggaatgttta ctacactcgg atatttgata tgtggatttc gagtcgtctt aatgtataga    1080
tttgaagaag agctgtttct gaggagcctt caggattaca agattcaaag tgcgctgctg    1140
gtgccaaccc tattctcctt cttcgccaaa agcactctga ttgacaaata cgatttatct    1200
aatttacacg aaattgcttc tggtggcgct cccctctcta aggaagtcgg ggaagcggtt    1260
gccaagaggt tccatctgcc aggtatcagg caaggatatg ggctcactga gactacatca    1320
gctattctga ttacacccga gggggatgat aaaccgggcg cggtcggtaa agttgttcca    1380
```

```
tttttttgaag cgaaggttgt ggatctggat accgggaaaa cgctgggcgt aatcaaaga   1440 ggcgaactgt gtgtgagagg tcctatgatt atgtccggtt atgtaaacaa tccggaagcg   1500
accaacgcct tgattgacaa ggatggatgg ctacattctg gagacatagc ttactgggac   1560
gaagacgaac acttcttcat cgttgaccgc ctgaagtctc tgattaagta caaaggctat   1620
caggtggctc ccgctgaatt ggaatccatc ttgctccaac accccaacat cttcgacgca   1680
ggtgtcgcag gtcttcccga cgatgacgcc ggtgaacttc ccgccgccgt tgttgttttg   1740
gagcacggaa agacgatgac ggaaaaagag atcgtggatt acgtcgccag tcaagtaaca   1800
accgcgaaaa agttgcgcgg aggagttgtg tttgtggacg aagtaccgaa aggtcttacc   1860
ggaaaactcg acgcaagaaa aatcagagag atcctcataa aggccaagaa gggcggaaag   1920
atcgccgtgt aattctagag tcggggcggc cggccgcttc gagcagacat gataagatac   1980
attgatgagt ttggacaaac cacaactaga atgcagtgaa aaaaatgctt tatttgtgaa   2040
atttgtgatg ctattgcttt atttgtaacc attataagct gcaataaaca agttaacaac   2100
aacaattgca ttcattttat gtttcaggtt caggggagg tgtgggaggt tttttaaagc   2160
aagtaaaacc tctacaaatg tggtaaaatc gataaggatc cgtcgaccga tgcccttgag   2220
agccttcaac ccagtcagct ccttccggtg gcgcggggc atgactatcg tcgccgcact   2280
tatgactgtc ttctttatca tgcaactcgt aggacaggtg ccggcagcgc tcttccgctt   2340
cctcgctcac tgactcgctg cgctcggtcg ttcggctgcg gcgagcggta tcagctcact   2400
caaaggcggt aatacggtta tccacagaat caggggataa cgcaggaaag aacatgtgag   2460
caaaaggcca gcaaaaggcc aggaaccgta aaaaggccgc gttgctggcg ttttttccata   2520 ggctccgccc cctgacgag catcacaaaa atcgacgctc aagtcagagg tggcgaaacc   2580
cgacaggact ataaagatac caggcgtttc ccctggaag ctccctcgtg cgctctcctg   2640
ttccgacccc tgccgcttac cggatacctgt ccgcctttct cccttcggga agcgtggcgc   2700
tttctcatag ctcacgctgt aggtatctca gttcggtgta ggtcgttcgc tccaagctgg   2760
gctgtgtgca cgaacccccc gttcagcccg accgctgcgc cttatccggt aactatcgtc   2820
ttgagtccaa cccggtaaga cacgacttat cgccactggc agcagccact ggtaacagga   2880
ttagcagagc gaggtatgta ggcggtgcta cagagttctt gaagtggtgg cctaactacg   2940
gctacactag aagaacagta tttggtatct gcgctctgct gaagccagtt accttcggaa   3000
aaagagttgg tagctcttga tccggcaaac aaaccaccgc tggtagcggt ggtttttttg   3060
tttgcaagca gcagattacg cgcagaaaaa aaggatctca agaagatcct ttgatctttt   3120
ctacggggtc tgacgctcag tggaacgaaa actcacgtta agggattttg gtcatgagat   3180
tatcaaaaag gatcttcacc tagatccttt taaattaaaa atgaagtttt aaatcaatct   3240
aaagtatata tgagtaaact tggtctgaca gttaccaatg cttaatcagt gaggcaccta   3300
tctcagcgat ctgtctattt cgttcatcca tagttgcctg actccccgtc gtgtagataa   3360
ctacgatacg ggagggctta ccatctggcc ccagtgctgc aatgataccg cgagacccac   3420
gctcaccggc tccagattta tcagcaataa accagccagc cggaagggcc gagcgcagaa   3480
gtggtcctgc aactttatcc gcctccatcc agtctattaa ttgttgccgg gaagctagag   3540
taagtagttc gccagttaat agtttgcgca acgttgttgc cattgctaca ggcatcgtgg   3600
tgtcacgctc gtcgtttggt atggcttcat tcagctccgg ttcccaacga tcaaggcgag   3660
ttacatgatc ccccatgttg tgcaaaaaag cggttagctc cttcggtcct ccgatcgttg   3720
tcagaagtaa gttggccgca gtgttatcac tcatggttat ggcagcactg cataattctc   3780
```

-continued

```
ttactgtcat gccatccgta agatgctttt ctgtgactgg tgagtactca accaagtcat    3840
tctgagaata gtgtatgcgg cgaccgagtt gctcttgccc ggcgtcaata cgggataata    3900
ccgcgccaca tagcagaact ttaaaagtgc tcatcattgg aaaacgttct cggggcgaa     3960 aactctcaag gatcttaccg ctgttgagat ccagttcgat gtaacccact cgtgcaccca    4020
actgatcttc agcatctttt actttcacca gcgtttctgg gtgagcaaaa acaggaaggc    4080
aaaatgccgc aaaaagggaa taagggcga cacggaaatg ttgaatactc atactcttcc    4140 ttttcaata ttattgaagc atttatcagg gttattgtct catgagcgga tacatatttg     4200
aatgtattta gaaaaataaa caatagggg ttccgcgcac atttccccga aaagtgccac     4260
ctgacgcgcc ctgtagcggc gcattaagcg cggcgggtgt ggtggttacg cgcagcgtga    4320
ccgctacact gccagcgccc ctagcgcccg ctcctttcgc tttcttccct tcctttctcg    4380
ccacgttcgc cggctttccc cgtcaagctc taaatcgggg gctcccttta gggttccgat    4440
ttagtgcttt acggcacctc gaccccaaaa aacttgatta gggtgatggt tcacgtagtg    4500
ggccatcgcc ctgatagacg gttttcgcc ctttgacgtt ggagtccacg ttctttaata     4560
gtggactctt gttccaaact ggaacaacac tcaaccctat ctcggtctat tctttgatt     4620 tataagggat tttgccgatt tcggcctatt ggttaaaaaa tgagctgatt taacaaaaat    4680
ttaacgcgaa ttttaacaaa atattaacgc ttacaatttg ccattcgcca ttcaggctgc    4740
gcaactgttg ggaagggcga tcggtgcggg cctcttcgct attacgccag cccaagctac    4800
catgataagt aagtaatatt aaggtacggg aggtacttgg agcggccgca ataaaatatc    4860
tttattttca ttacatctgt gtgttggttt tttgtgtgaa tcgatagtac taacatacgc    4920
tctccatcaa aacaaaacga aacaaaacaa actagcaaaa taggctgtcc ccagtgcaag    4980
tgcaggtgcc agaacatttc tctatcgata                                     5010
```

<210> SEQ ID NO 2
<211> LENGTH: 28
<212> TYPE: DNA
<213> ORGANISM: Artificial
<220> FEATURE:
<223> OTHER INFORMATION: RTP801 forward primer

<400> SEQUENCE: 2
gaagatctag ctttaggatc caagacgc                                        28

<210> SEQ ID NO 3
<211> LENGTH: 28
<212> TYPE: DNA
<213> ORGANISM: Artificial
<220> FEATURE:
<223> OTHER INFORMATION: RTP801 backward primer

<400> SEQUENCE: 3
cccaagcttg gtgaggacag acgccagg                                        28

<210> SEQ ID NO 4
<211> LENGTH: 28
<212> TYPE: DNA
<213> ORGANISM: Artificial
<220> FEATURE:
<223> OTHER INFORMATION: RTP801-645 forward primer

<400> SEQUENCE: 4
gaagatctct ggtcacgggc tgtcccct                                        28

<210> SEQ ID NO 5
<211> LENGTH: 28
<212> TYPE: DNA
<213> ORGANISM: Artificial
<220> FEATURE:
<223> OTHER INFORMATION: RTP801-545 forward primer

<400> SEQUENCE: 5
gaagatctct gcagccgccg cggatcct                                28

<210> SEQ ID NO 6
<211> LENGTH: 28
<212> TYPE: DNA
<213> ORGANISM: Artificial
<220> FEATURE:
<223> OTHER INFORMATION: RTP801-495 forward primer

<400> SEQUENCE: 6
gaagatctgg ttcgactgcg agctttct                                28

<210> SEQ ID NO 7
<211> LENGTH: 28
<212> TYPE: DNA
<213> ORGANISM: Artificial
<220> FEATURE:
<223> OTHER INFORMATION: RTP801-445 forward primer

<400> SEQUENCE: 7
gaagatctgt caccgggcag gagagaac                                28

<210> SEQ ID NO 8
<211> LENGTH: 28
<212> TYPE: DNA
<213> ORGANISM: Artificial
<220> FEATURE:
<223> OTHER INFORMATION: RTP801-395 forward primer

<400> SEQUENCE: 8
gaagatctca aggcgggcca cactcccg                                28

<210> SEQ ID NO 9
<211> LENGTH: 34
<212> TYPE: DNA
<213> ORGANISM: Artificial
<220> FEATURE:
<223> OTHER INFORMATION: Sp1 mutant upstrand primer

<400> SEQUENCE: 9
ctggggctca atgGATTATG ggcccggccg ctgt                         34

<210> SEQ ID NO 10
<211> LENGTH: 34
<212> TYPE: DNA
<213> ORGANISM: Artificial
<220> FEATURE:
<223> OTHER INFORMATION: Sp1 downstrand primer

<400> SEQUENCE: 10
acagcggccg ggcccataat ccattgagcc ccag                         34

<210> SEQ ID NO 11
<211> LENGTH: 50
<212> TYPE: DNA
<213> ORGANISM: Homo sapiens -continued

```
<400> SEQUENCE: 11
ggttcgactg cgagctttct ggggctcaat ggaggcgggg cccggccgct          50

<210> SEQ ID NO 12
<211> LENGTH: 50
<212> TYPE: DNA
<213> ORGANISM: Artificial
<220> FEATURE:
<223> OTHER INFORMATION: Mutant Sp1 site

<400> SEQUENCE: 12
ggttcgactg cgagctttct ggggctcaat ggattatggg cccggccgct          50

<210> SEQ ID NO 13
<211> LENGTH: 4425
<212> TYPE: DNA
<213> ORGANISM: Artificial
<220> FEATURE:
<223> OTHER INFORMATION: Plasmid pRTP801-VEGF

<400> SEQUENCE: 13
ggtaccgagc tcttacgcgt gctagcccgg gctcgagatc tagctttagg atccaagacg    60
ctgggggcaa ccattttcct tgcccgccgc cccctcacgc ttccctgcct ctcctcctag   120
cctggtcacg gcctgtcccc tcctccagca atgcaaccct ataataaaca agtctttcct   180
tgatcctccc ctgccgcgag cgccctcggg gaccttggca gctgcagccg ccgcggatcc   240
tttccagaaa gggggcgtgg cggtgggtcg ggttcgact gcgagctttc tggggctcaa   300
tggaggcggg gcccggccgc tgtcaccggg caggagagaa cgttgcttac gtgcgcccgg   360
agtccattgg ccaaggcggg ccacactccc gggtctggat tgggtcgtgg cgcagagaag   420
gcgtggcctc gccgcgctag tccttatagg ctgctccgcg ctggtgctag ggcgcagcag   480
gccaaggggg aggtgcgagc gtggacctgg gacgggtctg gcggctctc ggtggttggc   540 acgggttcgc acacccattc aagcggcagg acgcacttgt cttagcagtt ctcgctgacc   600
gcgctagctg gtgagtgtcc cttctgtgtg tgggtcctag agctcgcggt ctggtctggt   660
ctggtcccca gactgacgcc tggtcggtcc ccctcttgtc ttacagcggc ttctacgctc   720
cggcactctg agttcatcag caaacgccct ggcgtctgtc ctcaccaagc ttatgaactt   780
tctgctgtct tgggtgcatt ggagccttgc cttgctgctc tacctccacc atgccaagtg   840
gtcccaggct gcacccatgg cagaaggagg ggggcagaat catcacgaag tggtgaagtt   900
catggatgtc tatcagcgca gctactgcca tccaatcgag accctggtgg acatcttcca   960
ggagtaccct gatgagatcg agtacatctt caagccatcc tgtgtgcccc tgatgcgatg  1020 cggggctgc tgcaatgacg agggcctgga gtgtgtgccc actgaggagt ccaacatcac  1080
catgcagatt atgcggatca aacctcacca aggccagcac ataggagaga tgagcttcct  1140
acagcacaac aaatgtgaat gcagaccaaa gaaagataga gcaagacaag aaaatccctg  1200
tgggccttgc tcagagcgga gaaagcattt gtttgtacaa gatccgcaga cgtgtaaatg  1260
ttcctgcaaa aacacagact cgcgttcaa ggcgaggcag cttgagttaa acgaacgtac  1320
ttgcagatgt gacaagccga ggcggtgatc tagagtcggg cggccggcc gcttcgagca  1380 gacatgataa gatacattga tgagtttgga caaaccacaa ctagaatgca gtgaaaaaaa  1440
tgctttattt gtgaaatttg tgatgctatt gctttatttg taaccattat aagctgcaat  1500
aaacaagtta acaacaacaa ttgcattcat tttatgtttc aggttcaggg ggaggtgtgg  1560
gaggtttttt aaagcaagta aaacctctac aaatgtggta aaatcgataa ggatccgtcg  1620
```

```
accgatgccc ttgagagcct tcaacccagt cagctccttc cggtgggcgc ggggcatgac    1680
tatcgtcgcc gcacttatga ctgtcttctt tatcatgcaa ctcgtaggac aggtgccggc    1740
agcgctcttc cgcttcctcg ctcactgact cgctgcgctc ggtcgttcgg ctgcggcgag    1800
cggtatcagc tcactcaaag gcggtaatac ggttatccac agaatcaggg gataacgcag    1860
gaaagaacat gtgagcaaaa ggccagcaaa aggccaggaa ccgtaaaaag gccgcgttgc    1920
tggcgttttt ccataggctc cgcccccctg acgagcatca caaaaatcga cgctcaagtc    1980
agaggtggcg aaacccgaca ggactataaa gataccaggc gtttccccct ggaagctccc    2040
tcgtgcgctc tcctgttccg accctgccgc ttaccggata cctgtccgcc tttctccctt    2100
cgggaagcgt ggcgctttct catagctcac gctgtaggta tctcagttcg gtgtaggtcg    2160
ttcgctccaa gctgggctgt gtgcacgaac cccccgttca gcccgaccgc tgcgccttat    2220
ccggtaacta tcgtcttgag tccaacccgg taagacacga cttatcgcca ctggcagcag    2280
ccactggtaa caggattagc agagcgaggt atgtaggcgg tgctacagag ttcttgaagt    2340
ggtggcctaa ctacggctac actagaagaa cagtatttgg tatctgcgct ctgctgaagc    2400
cagttacctt cggaaaaaga gttggtagct cttgatccgg caaacaaacc accgctggta    2460
gcggtggttt ttttgtttgc aagcagcaga ttacgcgcag aaaaaaagga tctcaagaag    2520
atcctttgat cttttctacg gggtctgacg ctcagtggaa cgaaaactca cgttaaggga    2580
ttttggtcat gagattatca aaaaggatct tcacctagat ccttttaaat taaaaatgaa    2640
gttttaaatc aatctaaagt atatatgagt aaacttggtc tgacagttac caatgcttaa    2700
tcagtgaggc acctatctca gcgatctgtc tatttcgttc atccatagtt gcctgactcc    2760
ccgtcgtgta gataactacg atacgggagg gcttaccatc tggccccagt gctgcaatga    2820
taccgcgaga cccacgctca ccggctccag atttatcagc aataaaccag ccagccggaa    2880
gggccgagcg cagaagtggt cctgcaactt tatccgcctc catccagtct attaattgtt    2940
gccgggaagc tagagtaagt agttcgccag ttaatagttt gcgcaacgtt gttgccattg    3000
ctacaggcat cgtggtgtca cgctcgtcgt ttggtatggc ttcattcagc tccggttccc    3060
aacgatcaag gcgagttaca tgatcccccca tgttgtgcaa aaaagcggtt agctccttcg    3120
gtcctccgat cgttgtcaga agtaagttgg ccgcagtgtt atcactcatg gttatggcag    3180
cactgcataa ttctcttact gtcatgccat ccgtaagatg cttttctgtg actggtgagt    3240
actcaaccaa gtcattctga gaatagtgta tgcggcgacc gagttgctct tgcccggcgt    3300
caatacggga taataccgcg ccacatagca gaactttaaa agtgctcatc attggaaaac    3360
gttcttcggg gcgaaaactc tcaaggatct taccgctgtt gagatccagt tcgatgtaac    3420
ccactcgtgc acccaactga tcttcagcat cttttacttt caccagcgtt tctgggtgag    3480
caaaaacagg aaggcaaaat gccgcaaaaa agggaataag ggcgacacgg aaatgttgaa    3540
tactcatact cttccttttt caatattatt gaagcattta tcagggttat tgtctcatga    3600
gcggatacat atttgaatgt atttagaaaa ataaacaaat aggggttccg cgcacatttc    3660
cccgaaaagt gccacctgac gcgccctgta gcggcgcatt aagcgcggcg ggtgtggtgg    3720
ttacgcgcag cgtgaccgct acacttgcca gcgccctagc gcccgctcct ttcgctttct    3780
tcccttcctt tctcgccacg ttcgccggct ttccccgtca gctctaaat cggggctcc     3840 ctttagggtt ccgatttagt gctttacggc acctcgaccc caaaaaactt gattagggtg    3900
atggttcacg tagtgggcca tcgccctgat agacggtttt tcgccctttg acgttggagt    3960
ccacgttctt taatagtgga ctcttgttcc aaactggaac aacactcaac cctatctcgg    4020
```

-continued

```
tctattcttt tgatttataa gggattttgc cgatttcggc ctattggtta aaaaatgagc    4080
tgatttaaca aaaatttaac gcgaatttta acaaaatatt aacgcttaca atttgccatt    4140
cgccattcag gctgcgcaac tgttgggaag ggcgatcggt gcgggcctct tcgctattac    4200
gccagcccaa gctaccatga taagtaagta atattaaggt acgggaggta cttggagcgg    4260
ccgcaataaa atatctttat tttcattaca tctgtgtgtt ggtttttgt  gtgaatcgat    4320 agtactaaca tacgctctcc atcaaaacaa aacgaaacaa aacaaactag caaaataggc    4380
tgtccccagt gcaagtgcag gtgccagaac atttctctat cgata                   4425
```